(12) United States Patent
Carrison et al.

(10) Patent No.: US 6,878,151 B2
(45) Date of Patent: Apr. 12, 2005

(54) MEDICAL RETRIEVAL DEVICE

(75) Inventors: Harold F. Carrison, Pleasanton, CA (US); Roger D. Farnholtz, Fremont, CA (US); Linh To, San Jose, CA (US); Tra Huong Ngo, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 185 days.

(21) Appl. No.: 09/965,503

(22) Filed: Sep. 27, 2001

(65) Prior Publication Data

US 2003/0060833 A1 Mar. 27, 2003

(51) Int. Cl.[7] .................................................. A61F 11/00
(52) U.S. Cl. ........................................ 606/108; 606/200
(58) Field of Search ................................ 606/108, 200, 606/195

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 4,994,069 A | 2/1991 | Ritchart et al. |
| 5,064,428 A | 11/1991 | Cope et al. |
| 5,098,440 A | 3/1992 | Hillstead |
| 5,122,136 A | 6/1992 | Guglielmi et al. |
| 5,234,437 A | 8/1993 | Sepetka |
| 5,354,295 A | 10/1994 | Guglielmi et al. |
| 5,387,219 A | 2/1995 | Rappe |
| 5,486,183 A | 1/1996 | Middleman et al. |
| 5,522,819 A | 6/1996 | Graves et al. |
| 5,690,666 A | 11/1997 | Berenstein et al. |
| 5,826,587 A | 10/1998 | Berenstein et al. |
| 5,868,754 A | 2/1999 | Levine et al. |
| 5,895,398 A | 4/1999 | Wensel et al. |
| 5,944,728 A | 8/1999 | Bates |
| 6,001,118 A | 12/1999 | Daniel et al. |
| 6,066,149 A | 5/2000 | Samson et al. |
| 2002/0123720 A1 * | 9/2002 | Kusleika et al. ............ 604/108 |
| 2002/0151927 A1 * | 10/2002 | Douk et al. ................. 606/200 |
| 2002/0161389 A1 * | 10/2002 | Boyle et al. ................. 606/200 |
| 2002/0188314 A1 * | 12/2002 | Anderson et al. ........... 606/200 |
| 2002/0193824 A1 * | 12/2002 | Boylan et al. .............. 606/200 |

FOREIGN PATENT DOCUMENTS

WO    WO 93/00875    2/1993

\* cited by examiner

*Primary Examiner*—Eduardo C. Robert
(74) *Attorney, Agent, or Firm*—Crompton, Seager & Tufte LLC (57) ABSTRACT

Compositions comprising devices for retrieving objects from a subject, for example the subject's vasculature, are described. In particular, devices including a catheter shaft having a lumen through which a core wire extends are provided. Proximal and distal junction members are disposed around the core wire and at least one junction member is permanently and slidably attached to the core wire. In addition, the device includes a retrieval element as well as a stop element that is attached to the core wire distal to the catheter shaft. Also described are methods of making and using these devices.

29 Claims, 5 Drawing Sheets

MEDICAL RETRIEVAL DEVICE

FIELD OF THE INVENTION

The invention is in the field of surgery and medical devices. In particular, the invention is a device for capturing and removing foreign bodies or articles from within a vessel lumen or cavity.

BACKGROUND

Embolization in selected regions of the body is becoming of increasing therapeutic importance in treating conditions such as arteriovascular malformations, aneurysms, fistulas, vascular tumors, and the like. In some instances, the procedure involves placing foreign bodies such as metal coils, balloons, beads, and the like into the vessel. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. (See, e.g., U.S. Pat. No. 4,994,069 to Ritchart et al.) Other less stiff helically coiled devices have been described, as well as those involving woven braids.

U.S. Pat. No. 5,354,295 and its parent, U.S. Pat. No. 5,122,136, both to Guglielmi et al., describe an electrolytically detachable embolic device. Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

At times these bodies become errant or it is desired to retrieve and remove them from the vessel for other reasons. However, existing snares are sometimes too stiff or too large to permit deep tissue access through tortuous vessel paths. For instance, U.S. Pat. No. 5,098,440 is directed to a method and device for retrieving or repositioning a stent within a blood vessel. The apparatus includes a distal end with a loop for engaging the stent, a proximal end for manipulating the distal end and an intermediate portion that is shielded from the blood vessel by an elongated catheter.

PCT/US93/00875, filed Feb. 2, 1993, incorporated by reference in its entirety, is directed to a medical retrieval device with catheter and guidewire components. The distal end of the guidewire is coil-wrapped and forms a loop which is affixed to the distal end of the catheter. The size of the loop is altered by axial movement of the proximal portion of the guidewire.

Various configurations have been used to remove calculi from the biliary or urinary system. See, for instance, U.S. Pat. No. 5,064,428. Additionally, devices having various configurations have been used to remove objects from the vasculature. For example, surgical devices comprising one or more expandable and collapsible baskets have been described for removing or piercing a thrombus in the vasculature. See, U.S. Pat. Nos. 6,066,149. 5,868,754 describes a three prong-shaped device for capturing and removing bodies or articles from within a vessel.

None of the above documents show a device as described herein which includes a stop element to help keep the retriever element in the desired position.

SUMMARY OF THE INVENTION

Thus, the present invention includes a device suitable for retrieving bodies or articles (e.g., vaso-occlusive coils, catheter tips, wire tips and the like) from either tortuous vascular structures or larger vessels, organs, or ducts. The device is easy to manipulate and will not kink. Methods of using and making these devices are also described.

In one aspect, the invention is a device comprising a core wire having a distal end and a proximal end; a catheter shaft having a proximal catheter end, a distal catheter end and a lumen through which the core wire is passed such that the distal end of the core wire extends beyond the distal catheter end; a retrieval element, preferably attached to the core wire and a stop element that acts to limit expansion and/or proximal and distal movement of the retrieval element. In certain embodiments, the device also includes a proximal junction member having a lumen through which the core wire is passes such that the proximal junction member is disposed around the core wire distal to the distal catheter end; a distal junction member having a lumen through which the core is passed such that the distal junction member is disposed around the core wire distal to the proximal junction member; a retrieval element (e.g, a collapsible basket or other structure) and at least one stop element. In certain embodiments, the retrieval element comprises a first end attached to the proximal junction member and a second end attached to the distal junction member. In still further embodiments, a structure is attached to the distal end of the core wire. In certain embodiments, the core wire extends beyond the proximal catheter end.

In certain embodiments, the stop element comprises an inner stop, for example an inner stop attached to the core wire and positioned between said proximal and distal junctions. When present, an inner stop is preferably sized so that it cannot pass through the lumens of the proximal or distal junction members. Alternatively, the stop element can be external to the collapsible basket, so long as it functions to prevent or reduce over-expansion, collapse of the retrieval element and/or to keep the retrieval element in the desired position.

In embodiments in which the retrieval element comprises a basket structure, the basket can be made of a plurality of ribbons and/or wires wound into a braid, for example platinum-wrapped nitinol wires wound into a braid. Preferably, the first and second ends of the ribbons and/or wires making the basket are attached to the proximal and distal junction members, respectively. The distal and proximal junction members can be, for example, made out of carbothane.

Preferably, the structure (e.g., coil) attached to the distal end of the core wire is sized so that it cannot pass through the lumen of the distal junction member.

In another aspect, any of the devices described herein can further comprise one or more actuator handles and/or one or more torquer handles. In certain embodiments, an actuator handle is positioned (e.g., connected) near or at the proximal catheter end. Similarly, the torquer handle can be positioned (e.g., connected) near or at the proximal end of the core wire. The actuator handle can comprise, for example, a rotating hemostatic valve.

In yet another aspect, any of the devices described herein further comprise a radio-opaque material. In certain embodiments, one or more of the retrieval element (e.g., basket); the structure attached to the distal end of the core wire; the stop element; the core wire; and/or the catheter comprise a radio-opaque material. In certain embodiments, the radio-opaque material is gold, platinum, tantalum or combinations thereof.

In a further aspect, the invention includes a method for removing or repositioning a foreign body within a subject comprising the steps of: (i) introducing any of the devices described herein into the vasculature;(ii) moving the device near the foreign body; and (iii) manipulating the device to entrap the foreign body; and (iv) moving the device and entrapped foreign body to reposition or remove the foreign body. In certain embodiments, the manipulation comprises extending and retracting the core wire to collapse and expand the basket. Additionally, the manipulation can also include moving the assembly while maintaining the basket in a collapsed or expanded position. By using any combination of these manipulation techniques, the foreign body can be repositioned (e.g., pushed or pulled in a proximal or distal direction relative to the device) or removed, for example while keeping the basket expanded. In any of the methods described herein, the foreign body can be entrapped within the basket assembly. Further in any of the methods described herein, the foreign body can be, for example, a vaso-occlusive coil or a catheter shaft.

These and other embodiments of the subject invention will readily occur to those of skill in the art in light of the disclosure herein.

DESCRIPTION OF THE INVENTION

Surgical devices are described. The devices described herein find use in vascular and neurovascular indications and are particularly useful in treating aneurysms and embolisms, for example in small-diameter, curved or otherwise difficult to access vasculature. Methods of making and using these devices also aspects of this invention.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a basket" includes a two or more such baskets and the like.

The device is a surgical implement. It is designed to remove or reposition implantable medical devices situated in human vasculature. It is suitably flexible to be placed in the distal tortuous vasculature of the brain and hence is useful in removing and/or repositioning implantable medical devices such as vaso-occlusive coils.

Depicted in the Figures are exemplary embodiments of the present invention in which the retrieval element shown in the Figures is a collapsible basket structure. However, it will be appreciated that this is for purposes of demonstration only and that the retrieval element can have virtually any suitable shape, for example a prong shape as described in U.S. Pat. No. 5,868,754, coil shape, or the like.

Figure 1:
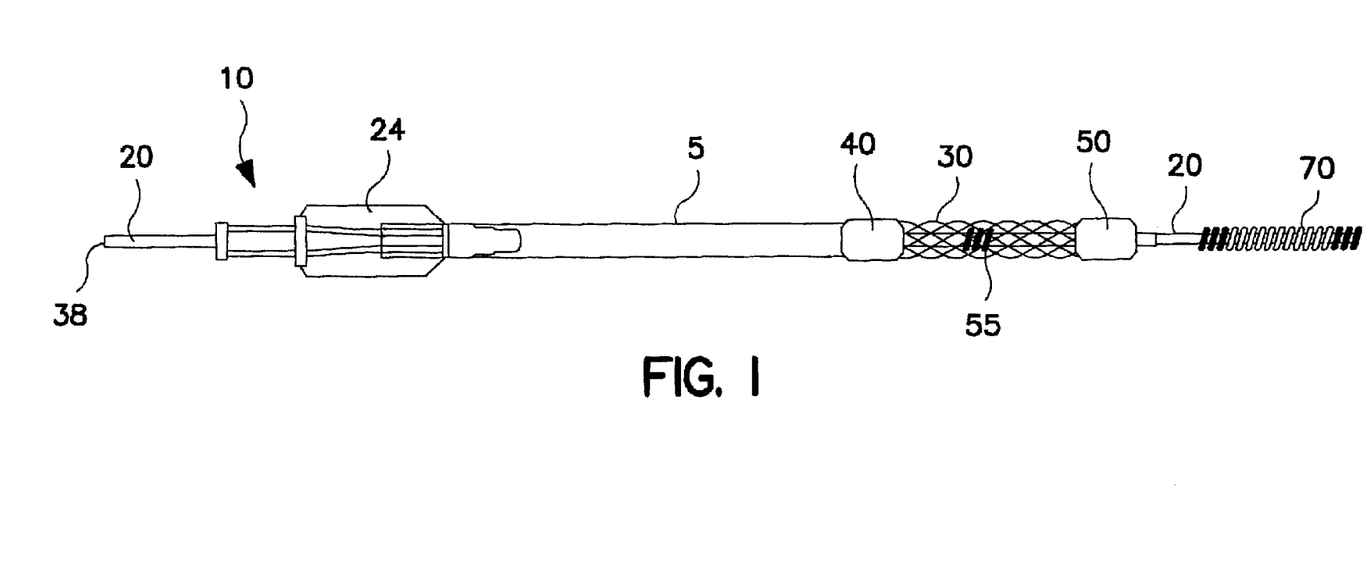
FIG. 1 depicts one embodiment of the medical retrieval device of the present invention.

FIG. 1 depicts a one exemplary embodiment of the inventive retrieval device which uses a collapsible basket as the retrieval element. The retrieval device as a whole is generally designated (10). Its principal components are: a catheter shaft (5); an actuator member (20) (in this case a movable core (or control) wire (20)); a retrieval element (e.g, basket) (30) attached to distal and proximal junction members distal to the catheter shaft; and an inner stop (55) disposed around the core wire between the distal and proximal junction members.

The core wire (20) is shown in the lumen of the catheter shaft (5). By "wire" is meant any filamentary shape having a cross-section where the thickness to width ratio is preferably between 0.5 including 1.0. The cross-sectional form may be circular, square, oval, etc. As described further below, the arrangement of the core wire is such that advancement of the core wire (20) causes extension of the basket (30), e.g., by causing the inner stop (55) to push against the distal junction of the basket and effecting extension of the basket. When the core wire (20) is retracted, the coil (70) distal to the basket (30) pushes on the distal junction of the basket (30) causing the diameter of the basket to increase. An actuator handle (28) is shown connected near the proximal end (38) of the wire (20) and can act as a handle for the attending physician to pull on the control wire (20) and to actuate the assembly. The core wire, actuator and retrieval elements will interact similarly when the retrieval element has a shape different from that of a basket, for example a cup or prong like retrieval element can be actuated in similar fashion.

The control wire (20), may be produced from any number of suitable materials having reasonable strength in tension, e.g., stainless steels, carbon fibers, engineering plastics, tungsten alloys, variously in the form of a multi-strand cable or single strand thread. Preferably, however, the core wire (20) is made from a "so-called" super-elastic alloy. These alloys are characterized by an ability to transform from an austenitic crystal structure to a stress-induced martensitic (SIM) structure and to return elastically to the austenitic crystal structure (and the original shape) when the stress is removed. A typical alloy is nitinol, a nickel-titanium alloy, which is readily commercially available and undergoes the austenite-SIM-austenite transformation at a variety of temperature ranges. These materials are described, for instance in U.S. Pat. Nos. 3,174,851 and 3,351,463. These alloys are especially suitable because of their capacity to elastically recover almost completely to the initial configuration once the stress is removed. Since this is so, the size of the actuator wire (20) may be made fairly small, e.g., as small as 0.005 inches in diameter, and the resulting device is able to access very small regions of the body. The wire may also vary in diameter along its length, for example have a larger diameter at the proximal end as compared to the distal end or vice versa. Choice of such alloys further allows the actuator members to undertake substantial stress in passing through the body's vasculature, and yet return to their original shape once the bend has been traversed without retaining any hint of a kink or bend.

The control wire (20) can have a proximal section and a distal section. The proximal section preferably has a uniform diameter of about 0.005 to 0.025 inches, preferably 0.010 to 0.018 inches. Optionally, the distal section may have different (more or less) flexibility than the proximal section and extends beyond the catheter. Typically, both sections will extend from the distal and proximal ends of the catheter lumen. The core wire (20) may have a middle section having a diameter intermediate between the diameter of the two portions of the wire adjoining the middle section or the middle section may be continuously tapered, may have a number of tapered sections or sections of differing diameters, or may be of a uniform diameter along its length and be tapered at or near the distal section. The entire actuator wire (20) may be between about 50 and 300 cm, typically between about 175 to 190 cm in length. As will be discussed below, the distal tip of the control wire may be wrapped to form a coil section or may be independently attached to a coil.

FIG. 1 also shows the overall length of the control wire (20), which extends through the catheter (5) and insert molded hub (24) to the distal end of the device. A collapsible basket (30) is positioned near the distal end of the core wire (20). Proximal junction (40) and distal junction (50) mark the boundaries of the basket (30). FIG. 1 shows the basket in a collapsed (extended) configuration.

The control wire (20) can also act as a guidewire and may be used to provide a pathway through tortuous vasculature for the device to follow. The control wire or other elements may be made of, or coated with, a material such as polytetrafluoroethylene (e.g., Teflon) and desirably extends all the way to the proximal end of the catheter. The core wire can be rotatable and axially moveable with respect to the basket assembly.

Preferably, the retrieval element aids in both engaging and moving the foreign body. As shown in the Figures, the retrieval element can be, for example, a basket element (30) that is disposed around the core wire and positioned to be distal to the distal end of the catheter shaft. The basket (30) is collapsible for passage in the vasculature and for capture, re-positioning and retrieval of the foreign bodies in the vasculature. Other retrieval structures such as prongs, wires, coils and the like can also be moveable and/or expandable for passage in the vasculature and for capture, re-positioning and retrieval of foreign bodies. There may be one or more retrieval elements of the same or of different configurations. In preferred embodiments, the movement (e.g., expansion) of this element is controlled by the operator's movement of the core wire (20), for example via one or more handles (24 and 28). For example, when using a collapsible basket structure, it is preferable that the basket is collapsed (extended) before insertion and during removal of the assembly. As can be seen by comparing FIGS. 3 and 4, retracting the core wire causes expansion the basket (30) by pulling the coil attached to the distal end of the control wire (20) toward the proximal end of the device. Thus, once a foreign body has been captured by the assembly, partial or complete expansion and/or movement of the retrieval element can re-position the body in situ. As will be apparent, the foreign body can also be completely removed by removing the entire device and captured foreign body.

Figure 2:
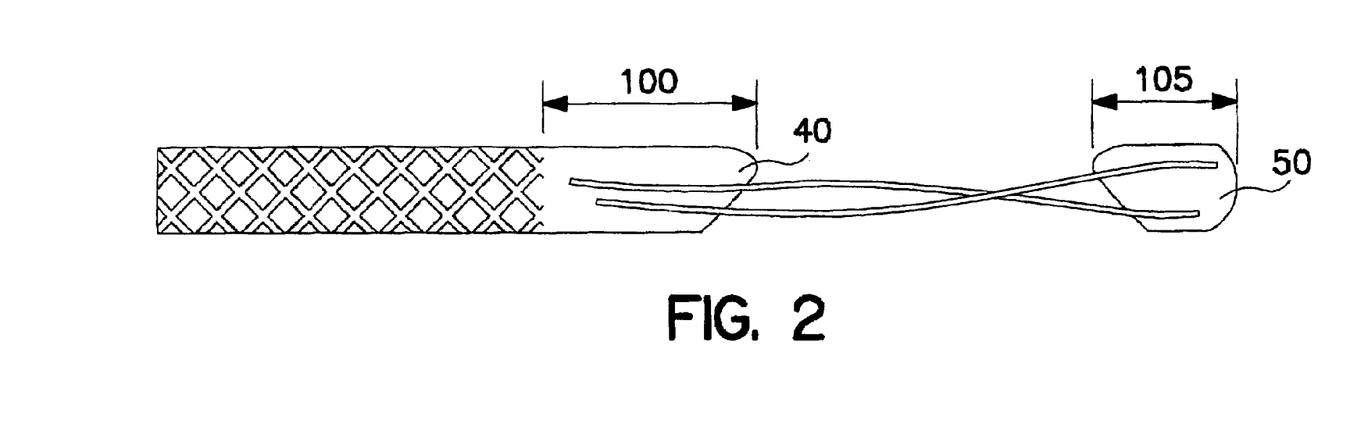
FIG. 2 depicts shows a detailed view of the connection between the wires or ribbons making up the basket and the distal and proximal junction members of the inventive device.

Basket (30) is preferably a cage-like structure comprising wires or ribbons, for example as a braided structure. FIG. 2 is a detail showing the junction between the basket assembly and the rest of the device. The proximal basket junction length (100) and distal basket junction length (105) are depicted by double-sided arrows. The Figure shows only two strands of the basket and how they are embedded in the proximal (40) and distal (50) junctions. Other retrieval elements are described, for example, in U.S. Pat. No. 5,868,754.

The proximal (40) and distal (50) junctions can be composed of any material. In a preferred embodiment, the junctions are comprised of carbothane. The junctions (40 and 50) also have a lumen large enough to fit the tapered end of the core wire (20), but not large enough to allow the inner stop (55) or the coil to pass through either junction. As shown in the Figures, in preferred embodiments, the proximal junction (40) is either directly adjacent to the distal end of the catheter shaft (5). Alternatively the assembly can be produced so that the proximal junction (40) is an integral part of the distal tip of the catheter shaft (5). Other configurations in which the proximal junction is completely distinct from the catheter shaft (5) are also contemplated.

The component wires and ribbons of a basket retrieval element (30) can be nitinol, stainless steel, platinum, gold, or alloys thereof and are typically between about 0.5 and 4 cm in length, as measured from distal end to proximal end when the ends are embedded in the distal and proximal junctions, respectively. By the term "ribbon", is meant any elongated shape, the cross section of which are not square or round and may typically be rectangular, oval, or semi-oval. They should have an aspect ratio of 0.5 (thickness/width) or less. In certain embodiments, the cage is made at least partially of a super-elastic alloy wires or ribbons. Some stainless steels or other such alloys also may be suitable. Although wires may be preferably, in certain embodiments ribbons of varying thicknesses and widths may also be suitable. A desirable variant is the substitution of one or more ribbons or wires (or the addition of one or more wires) with a radio-opaque material such as platinum which permits the user to visualize the position of the basket during a procedure. In a preferred embodiment, the platinum is wound around or coated onto the wires making up the basket.

The basket (30) may be made any suitable techniques including, but not limited to, injection molding, winding or the like. For example, a ribbon or a wire can be wound or braided onto a mandrel having an exterior form to produce the flexible shape shown in the Figures. The mandrel and wound ribbon are preferably heated for a suitable period of time to produce an assembly which has the portrayed shape. For use in the middle cerebral artery (MCA), the outer diameter of the device after deployment need not be any larger than about 3 mm. It is desirable that the collapsed cage have a diameter no larger than about 1 mm. The expansion ratio between the collapsed and expanded cage typically need not be any more than about 3:1 to be effective in the MCA. Expansion ratios between 2:1 and 10:1 are appropriate in this invention. These ratios are suitable for each variation of the invention. The invention is not so limited, however.

An important feature of the inventive devices described herein is a stop or brake device which prevents over-expansion or collapse of the retrieval element. As shown as in FIGS. 3 and 4, the brake comprises an inner stop (55) disposed around the core wire and positioned within the basket such that it can travel only between the proximal (40) and distal (50) junctions as the core wire (20) is extended or retracted.

Figure 3:
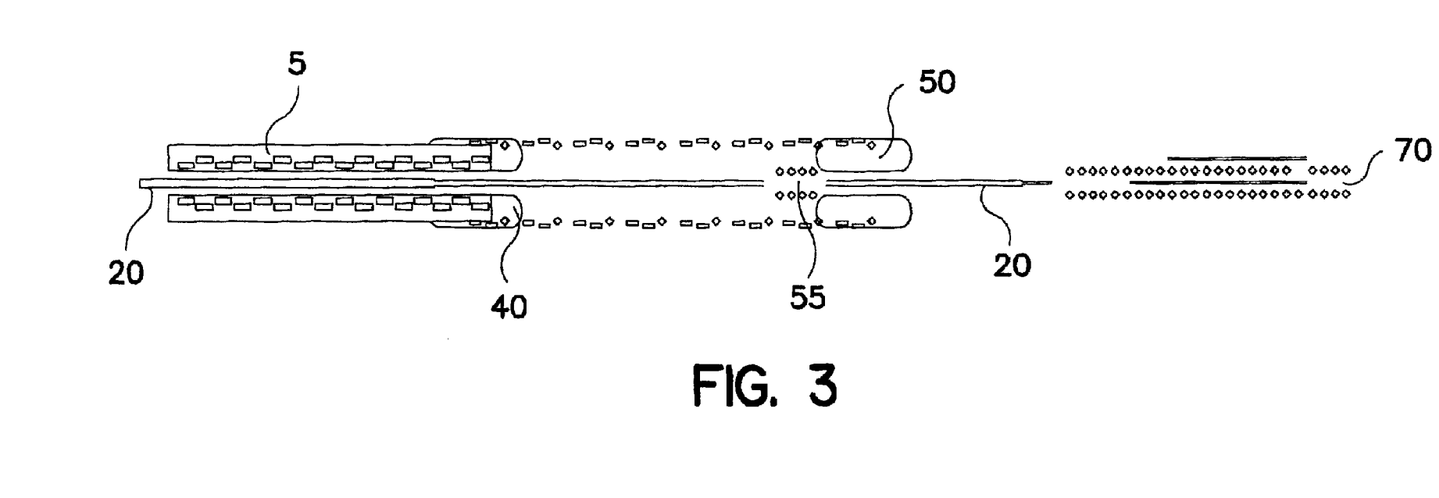
FIG. 3 depicts a view of the device in which the basket is collapsed (extended) by extending the core wire and causing the inner stop to push the distal junction member toward the distal end of the core wire.
Figure 4:
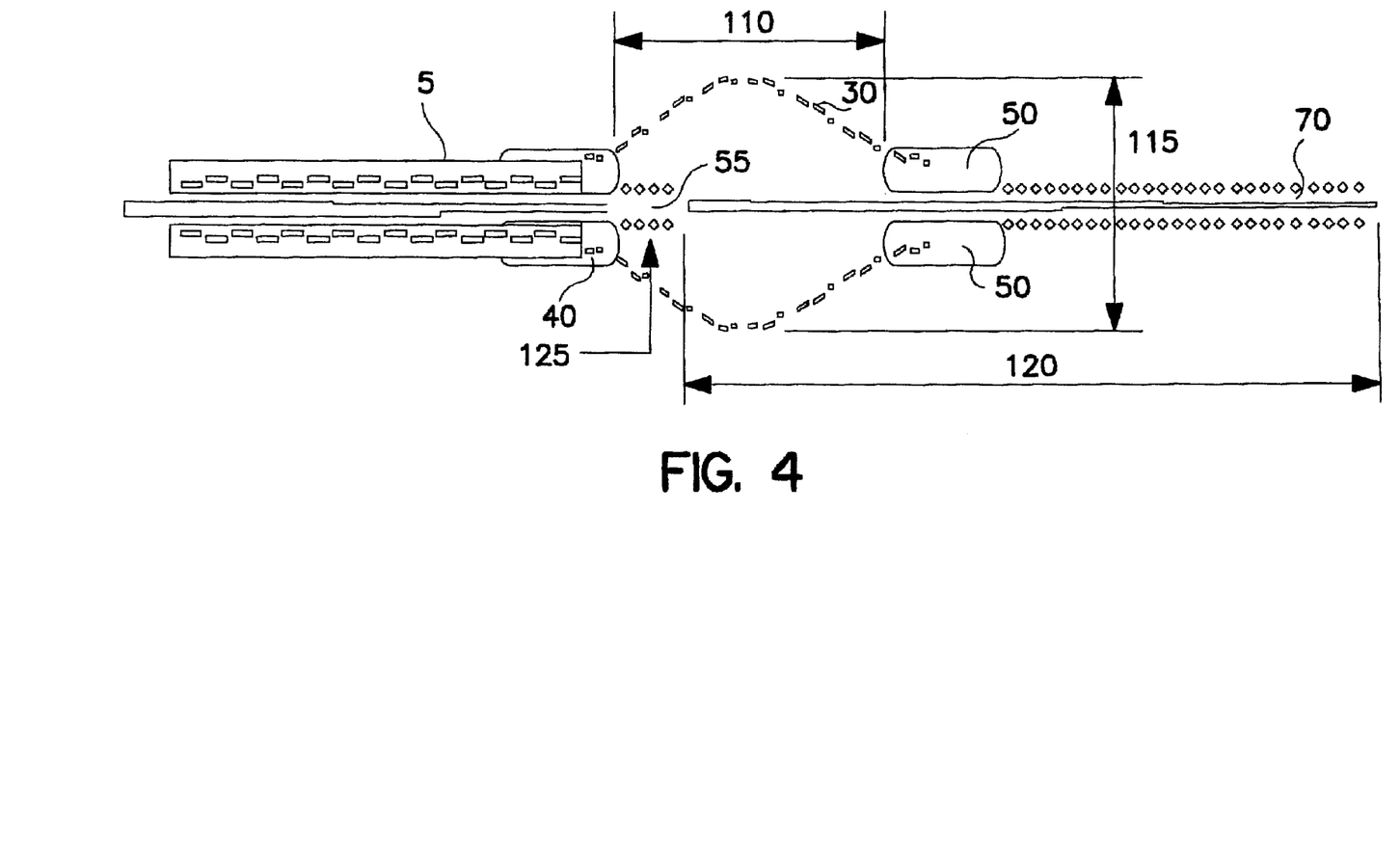
FIG. 4 depicts a view of the device in which the basket is expanded by retracting the core wire and causing the coil to push the distal junction member toward the proximal junction member. The inner stop prevents over-expansion.

Turning to embodiments in which the stop comprises an inner stop (5), FIGS. 3 and 4 illustrate how extension (out of the catheter shaft) of the core wire (20) causes the inner stop (55) to push against the distal junction member (50) and this in turn causes the basket (30) to collapse (extend). By the same token, retracting the core wire (20) causes the coil (70) at the distal end of the core wire to push against the distal junction member (50), which causes the basket (30) to expand as the distance between the two ends of the basket embedded in the junction members is decreased. Further, the inner stop (55) serves to prevent the expanded basket from over expanding (for example from turning inside-out). In particular, the inner stop acts as a brake by stopping movement of the distal junction member (50) as the core wire is retracted out of the proximal catheter end by the operator. As noted above, the inner stop (55) is preferably fixedly attached to the core wire in such a way so that it slides easily between the proximal (40) and distal (50) junctions as the basket (30) is expanded or collapsed by extension and retraction of the core wire (20). FIG. 4 also depicts the length (110) and outer diameter (115) of an expanded basket, as well as the distance (120) from the inner stop (55) to the tip and the outer diameter (125) of the inner stop junction.

The stop element can be made any material, for example, stainless steel, platinum, kevlar, PET, carbothane, cyanoacrylate, epoxy and mixtures or combinations of two or more of these.

As noted elsewhere, the location of the assembly should be visible using fluoroscopy. Various methods have been suggested above. One highly preferred method is to ensure that at least some of the elements (ribbons or wires) making up the basket are provided with significant radio-visibility via the placement of a radio-opaque covering on these elements. A metallic coating of a metal having comparatively more visibility, during fluoroscopic use, than stainless steel is preferred. Such metals are well-known but include gold and members of the Platinum Group of the Periodic Table, e.g., platinum, palladium, rhenium, rhodium, etc. The basket assembly wires or ribbons may be electroplated or otherwise provided with a continuous coating but a thick coating may be had by wrapping the element with a radio-opaque wire or ribbon.

A coil (70) is shown at the distal end of the control wire (20). Any suitable structure can be substituted for a coil, so long as it not harmful to the subject and so long as the structure cannot pass through the lumen of the distal junction member (50). In preferred embodiments, the coil (70) comprises any of the known vaso-occlusive coils, for example as described in U.S. Pat. No. 4,994,069 to Ritchart et al.; U.S. Pat. No. 5,354,295 and its parent, U.S. Pat. No. 5,122,136, both to Guglielmi et al.; and U.S. Pat. Nos. 5,690,666 and 5,826,587 by Berenstein et al. The coil is preferably fixedly attached to the distal end of the core wire. In preferred embodiments, the coil is at least partially radio-opaque for visualization in situ.

Figure 5:
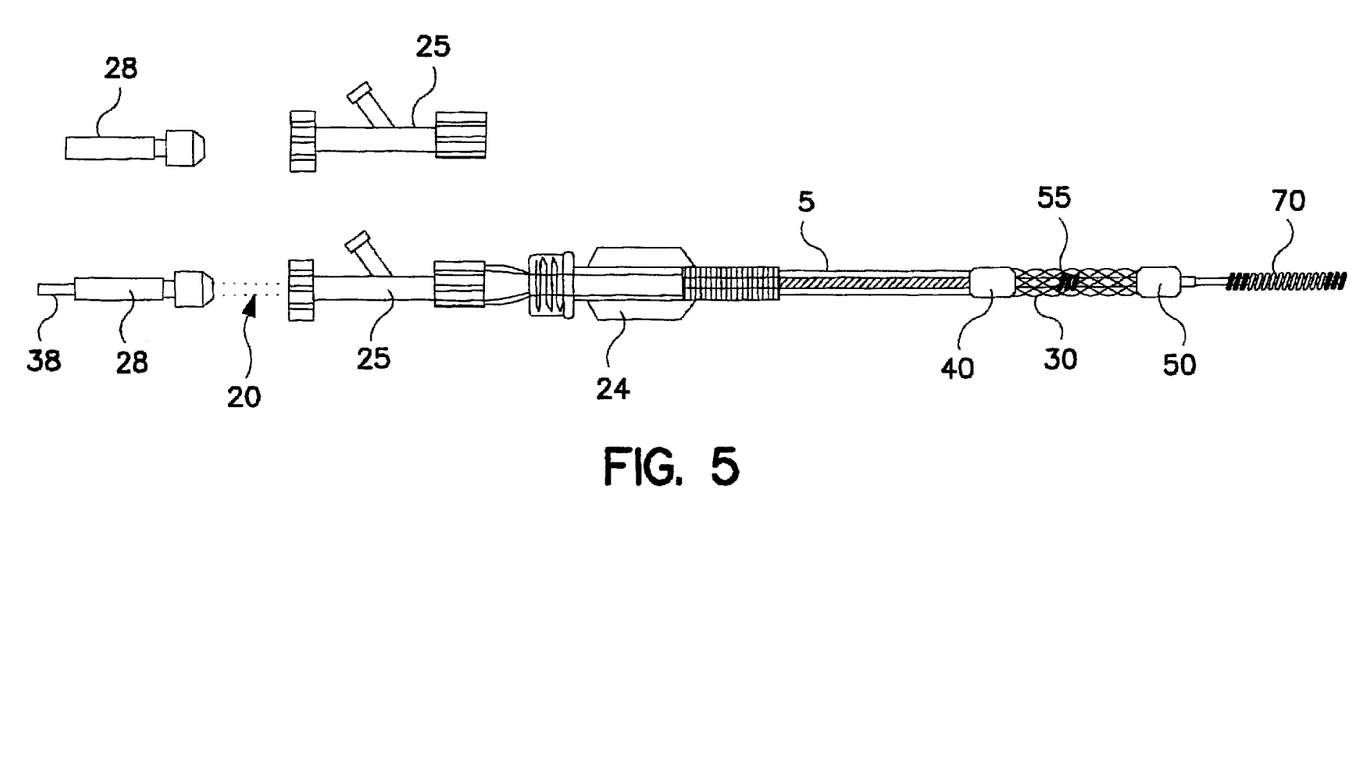
FIG. 5 depicts a view of an inventive device including actuator mechanisms near the proximal end of the device.

One or more actuating mechanisms are also preferably included, for example as shown in FIG. 5. Typically, a plurality of actuating components (24, 25 and 28) are included to act as actuator handles when activating the basket (30) via the control wire (20). One actuator component (28), also called a torquer, is accessible at the proximal end of the core wire (20) and is attached to the core wire. Although not necessary to control the operation of the basket (30), the torquer (28) allows the operator to have better control over the movement and/or rotation of the core wire (20). Thus, the lateral movement (e.g., extension and retraction) of the core wire (20) is limited by the basket junctions (40 and 50) and inner stop (55), while the rotational movement can be controlled via the torquer.

A second, often multi-component, actuator mechanism (24 and 25) is preferably found along the body of the catheter shaft (5). In certain embodiments, the catheter has an insert molded hub (24) located on or near the proximal end of the shaft. FIG. 5 also shows a catheter luer fitting (25) distal to the insert molded hub (24). Optionally, a device such as a rotating hemostatic valve (RHV) (25) is used to allow for the introduction of fluids and prevent the escape of blood during clinical application forms all or a portion of the second actuator. The actuating components may be overlapping or distinct. As will be readily apparent to those skilled in the art in view of the teachings herein, actuators may be made of any suitable material, although nature of the material is not critical here. Similarly the dimensions of the actuator(s) are not critical but can be readily be determined in view of the overall dimensions of the device.

To retrieve a body from within a vessel, the assembly is inserted into a vessel so that the distal end of the catheter is adjacent to the body to be removed from the vessel. The insertion of the assembly to such a location is accomplished in a conventional manner. As will be readily apparent to those skilled in the art, the target foreign body can be removed or repositioned in any number of ways by expanding and collapsing the basket via manipulation of the core wire (20). For example, to move a foreign body toward the assembly (e.g., proximally in the vessel), the assembly may be passed around (or through) the foreign body, typically while the basket is collapsed and the assembly is in a low-profile configuration. Once the coil and, preferably the basket, of the assembly are distal to the target foreign body, the operator can expand the basket by retracting the core wire. While keeping the basket expanded, the entire assembly can be moved proximally and the expanded basket will drag the foreign body in the desired, proximal direction. Alternatively, the basket can be opened while still proximal to the foreign body and the open-basket assembly used to push the foreign body in a distal direction.

It will also be apparent that the operator can remove or reposition (distally or proximally) a foreign body by trapping all or part of the foreign body within the basket or strands of the basket assembly. For instance, the operator may choose to insert the assembly with the basket collapsed and open the basket while the basket (and/or coil) is still proximal to the foreign body. The basket can be held open while the assembly is moved distally toward the foreign body which can then be trapped in the strands of the basket (or captured entirely within the basket) by closing the basket assembly. The operator can then reposition the foreign body by moving the assembly while holding the basket closed and keeping the foreign body entrapped therein. One or more of these steps can be combined and/or repeated until the foreign body is removed or reaches the desired position.

Thus, removal or repositioning of any foreign body is achieved by operation of the inventive assembly. At any point during this procedure, the operator can retract the core wire (20) to expand the basket or extend the core wire to collapse the basket. The inner stop (55) serves both to extend the basket (by pushing on the distal junction (50) until the basket is extended) and, additionally, to prevent over-expansion when the core wire is retracted.

In order to facilitate the axial manipulation of retrieval device within the catheter, a physiologically acceptable fluid may be pumped through the lumen of catheter and/or actuator with, for example, pumping means in conjunction with luer valve (25). Once the errant body (e.g., coil) is ensnared, axial movement of the core wire (20) and/or actuator components (24, 25, 28) repositions the body within the vessel and withdrawal of the catheter and retriever assembly from the vessel removes the body.

Although the Figures discussed above show a preferred variant of the retrieval device, many other useful configurations of the device are contemplated.

Modifications of the above-described variations of the invention that would be obvious to those of skill in the medical device art are intended to be within the scope of the following claims. These variations are intended to be within the scope of the claims that follow.

What is claimed is:

1. A device comprising
   a core wire having a distal end and a proximal end;
   a catheter shaft having a proximal catheter end, a distal catheter end and a lumen through which the core wire is passed such that the distal end of the core wire extends beyond the distal catheter end;
   a proximal junction member disposed around the core wire distal to the distal catheter end, wherein the proximal junction member has a lumen through which the core wire is passed;
   a distal junction member disposed around the core wire distal to the proximal junction member, wherein the distal junction member has a lumen through which the core wire is passed, wherein at least one of the proximal or distal junction members is permanently and slidably attached to the core wire;
   a structure attached to the distal end of the core wire, wherein said structure is sized so that it cannot pass through the lumen of the distal junction member;
   a retrieval element having two ends, wherein at least one end is attached to the distal or proximal junction member; and
   a stop element.

2. The device of claim 1, wherein the retrieval element comprises a collapsible basket having a first end attached to the proximal junction member and a second end attached to the distal junction member.

3. The device of claim 2, wherein the stop element comprises an inner stop attached to the core wire and positioned between said proximal and distal junctions, wherein said inner stop is sized so that it cannot pass through the lumens of the proximal or distal junction members.

4. The device of claim 2, wherein the basket comprises a plurality of ribbons or wires wound into a braid.

5. The device of claim 4, wherein the basket comprises a plurality of wires.

6. The device of claim 5, wherein the wires are platinum-wrapped nitinol.

7. The device of claim 4, wherein all of the ribbons or wires comprise first and second ends, wherein the first end is attached to the proximal junction member and the second end is attached to the distal junction member.

8. The device of claim 1, wherein the structure attached to the distal end of the core wire is a coil.

9. The device of claim 1, wherein the core wire extends beyond the proximal catheter end.

10. The device of claim 1, further comprising an actuator handle.

11. The device of claim 1, wherein the distal and proximal junction members are carbothane.

12. The device of claim 1, further comprising a radio-opaque material.

13. The device of claim 12, wherein the retrieval element further comprises a radio-opaque material.

14. The device of claim 12, wherein the stop element comprises a radio-opaque material.

15. The device of claim 12, wherein the radio-opaque material is selected from the group consisting of gold, platinum or tantalum.

16. The device of claim 1, wherein the structure attached to the distal end of the core wire further comprises a radio-opaque material.

17. The device of claim 1, further comprising an actuator handle positioned near the proximal catheter end.

18. The device of claim 17, wherein the actuator handle comprises a rotating hemostatic valve.

19. The device of claim 1, further comprising a torquer handle connected near the proximal end of the core wire.

20. A method for removing or repositioning a foreign body within a subject, the method comprising the steps of:
   (i) introducing a device according to claim 1 into the vasculature;
   (ii) moving the device near the foreign body; and
   (iii) manipulating the device to entrap the foreign body; and
   (iv) moving the device and entrapped foreign body to reposition or remove the foreign body.

21. The method of claim 20, wherein retrieval element of the device comprises a collapsible basket.

22. The method of claim 21, wherein the manipulation comprises extending and retracting the core wire to collapse and expand the basket.

23. The method of claim 22, wherein the manipulation further comprises moving the device while maintaining the basket in a collapsed or expanded position.

24. The method of claim 21, the manipulation comprises retracting the core wire to expand the basket and wherein the foreign body is pushed or pulled by the expanded basket upon movement of the device in a distal or proximal direction.

25. The method of claim 24, wherein the foreign body is pushed by the basket upon moving the device in the distal direction.

26. The method of claim 24, wherein device is positioned distal to the foreign body prior to expansion of the basket and wherein the foreign body is pulled by the basket upon moving the device in the proximal direction.

27. The method of claim 20, wherein the foreign body is entrapped within the retrieval element.

28. The method of claim 20, further comprising withdrawing said device with entrapped foreign body from the vasculature, thereby removing the foreign body.

29. The method of claim 20, wherein the foreign body comprises a vaso-occlusive coil or a catheter shaft.

* * * * *

UNITED STATES PATENT AND TRADEMARK OFFICE
CERTIFICATE OF CORRECTION

PATENT NO.       : 6,878,151 B2                                      Page 1 of 1
APPLICATION NO.  : 09/965503
DATED            : April 12, 2005
INVENTOR(S)      : Harold F. Carrison et al.

It is certified that error appears in the above-identified patent and that said Letters Patent is hereby corrected as shown below:

Col. 10 Claim 24, line 37, after "claim 21,", add --wherein--

Signed and Sealed this

Twenty-sixth Day of December, 2006

JON W. DUDAS
*Director of the United States Patent and Trademark Office*